United States Patent
Gross et al.

(10) Patent No.: US 10,842,169 B2
(45) Date of Patent: Nov. 24, 2020

(54) PET FOOD COMPOSITION FOR MANAGING NON-FOOD ALLERGIES

(71) Applicant: Hill's Pet Nutrition, Inc., Topeka, KS (US)

(72) Inventors: Kathy Gross, Topeka, KS (US); Jennifer Macleay, Topeka, KS (US); Dale Allen Fritsch, Topeka, KS (US); Geoff Bednar, Lawrence, KS (US); Kiran Panickar, Lawrence, KS (US); Inke Paetau-Robinson, Auburn, KS (US); Dennis Jewell, Lawrence, KS (US)

(73) Assignee: Hill's Pet Nutrition, Inc., Topeka, KS (US)

( * ) Notice: Subject to any disclaimer, the term of this patent is extended or adjusted under 35 U.S.C. 154(b) by 206 days.

(21) Appl. No.: 15/764,345

(22) PCT Filed: Apr. 22, 2016

(86) PCT No.: PCT/US2016/029013
§ 371 (c)(1),
(2) Date: Mar. 29, 2018

(87) PCT Pub. No.: WO2017/058291
PCT Pub. Date: Apr. 6, 2017

(65) Prior Publication Data
US 2018/0279648 A1 Oct. 4, 2018

Related U.S. Application Data

(60) Provisional application No. 62/235,082, filed on Sep. 30, 2015.

(51) Int. Cl.
*A23K 10/20* (2016.01)
*A23K 20/174* (2016.01)
*A23K 20/111* (2016.01)
*A23K 20/158* (2016.01)
*A23K 50/40* (2016.01)

(52) U.S. Cl.
CPC ............ *A23K 10/20* (2016.05); *A23K 20/111* (2016.05); *A23K 20/158* (2016.05); *A23K 20/174* (2016.05); *A23K 50/40* (2016.05)

(58) Field of Classification Search
None
See application file for complete search history.

(56) References Cited

U.S. PATENT DOCUMENTS

| | | | |
|---|---|---|---|
| 8,088,409 B2 | 1/2012 | Yamka | |
| 8,669,282 B2 | 3/2014 | Zicker | |
| 2003/0144219 A1* | 7/2003 | Phinney | A61K 31/202 514/27 |
| 2008/0233244 A1* | 9/2008 | Swenson | A23J 3/16 426/72 |
| 2013/0216521 A1* | 8/2013 | Culver | A61K 36/899 424/130.1 |
| 2017/0079947 A1* | 3/2017 | Richards | A61P 11/06 |

FOREIGN PATENT DOCUMENTS

| | | |
|---|---|---|
| EP | 0678247 A1 * | 10/1995 |
| JP | H08-38063 | 2/1996 |
| JP | 2011-188832 | 9/2011 |
| JP | 2015-516372 | 6/2015 |
| WO | 1999/062201 | 12/1999 |
| WO | 1999/065514 | 12/1999 |
| WO | 2010/122104 | 10/2010 |
| WO | 2011/087706 | 7/2011 |

OTHER PUBLICATIONS

Karakaya et al., "Quercetin, luteolin, apigenin and kaempferol contents of some foods", 1999, vol. 66, Issue 3, pp. 289-292.*
International Search Report and Written Opinion of the International Searching Authority in International Application No. PCT/US2016/029013, dated Aug. 31, 2016.

* cited by examiner

Primary Examiner — Robert A Wax
Assistant Examiner — Randeep Singh

(57) ABSTRACT

A food composition for managing non-food allergies in companion animals is disclosed, along with a method of managing non-food allergies.

20 Claims, 6 Drawing Sheets

PET FOOD COMPOSITION FOR MANAGING NON-FOOD ALLERGIES

CROSS-REFERENCE TO RELATED APPLICATIONS

This application claims the benefit of U.S. Provisional Application No. 62/235,082, filed on Sep. 30, 2015. The disclosure of the above application is incorporated herein by reference.

BACKGROUND

Approximately 15-25% of all small animal veterinary practice activity is devoted to problems related to the skin and coat of dogs and cats (Small Animal Clinical Nutrition 5th Edition p. 637). Allergies in pets can be caused by foods (chicken, beef, dairy, soy, etc.) and by non-food causes including environmental elements like pollens, dusts, molds, mites, flea bites, etc. ("environmental allergies"). Among pets with allergies, approximately 80% have environmental allergies, and 20% have food allergies. For pets with food allergies, diets are commonly available that lack specific ingredients known to cause allergic reactions, e.g., chicken or beef.

Currently, a typical treatment for dogs displaying symptoms of environmental allergies includes the administration of steroids, anti-histamines, baths/dips, and/or nutritional supplements. There is a need for a less invasive, more natural approach to relieving the symptoms of environmental allergies. The invention addresses this need with a highly palatable and easy to feed food composition.

BRIEF SUMMARY

The invention is directed to a pet food composition for managing non-food allergies. The pet food composition comprises a combination of nutrients, including omega-6, omega-3, omega-9, alpha lipoic acid, quercetin sources including selected herbs, fruits and vegetables, egg product and vitamin E and C. Further, the invention is directed to the use of a pet food composition in managing non-food allergies in companion animals as part of a treatment regimen.

In an embodiment, compositions for managing non-food allergies in a companion animal are provided comprising: one or more omega-3 fatty acids, one or more omega-6 fatty acids, and one or more omega-9 fatty acids, in relative amounts to produce a total omega-3 to total omega-6 fatty acid to total omega-9 fatty acid ratio of from about 0.5:2.0:2.0 to about 3.0:5.0:5.0, and a total omega-6 fatty acid content of from about 1.5 percent by weight to about 12 percent by weight; from 0.1 percent by weight to 15 percent by weight of egg product; and alpha-lipoic acid; polyphenol; Vitamin C and Vitamin E are present in therapeutic non-zero amounts, wherein all percentages by weight are based on total dry weight.

In an embodiment, compositions for managing non-food allergies in a companion animal are provided comprising: one or more omega-3 fatty acids, one or more omega-6 fatty acids, and one or more omega-9 fatty acids, in relative amounts to produce a total omega-3 to total omega-6 fatty acid to total omega-9 fatty acid ratio of from about 0.9:2.0:2.0 to about 3.0:5.0:5.0, and a total omega-6 fatty acid content of from about 1.5 percent by weight to about 12 percent by weight; from 0.01 percent by weight to 0.12 percent by weight alpha-lipoic acid; from 0.1 percent by weight to 15 percent by weight of egg product; from 200 IU/kg to 1,300 IU/kg Vitamin E; from 30 ppm to 750 ppm Vitamin C; and from 1.5 ppm to 50 ppm polyphenol; wherein, all percentages by weight are based on total dry weight.

Another embodiment provides a method for managing allergies to non-food allergens in a companion animal comprising feeding the animal during an induction period prior to exposure of the animal to the non-food allergen with a food composition comprising: one or more omega-3 fatty acids, one or more omega-6 fatty acids, and one or more omega-9 fatty acids, in relative amounts to produce a total omega-3 to total omega-6 fatty acid to total omega-9 fatty acid ratio of from about 0.9:2.0:2.0 to about 3.0:5.0:5.0, and a total omega-6 fatty acid content of from about 1.5 percent by weight to about 12 percent by weight; from 0.01 percent by weight to 0.12 percent by weight alpha-lipoic acid; from 0.1 percent by weight to 15 percent by weight of egg product; from 200 IU/kg to 1,300 IU/kg Vitamin E; from 30 ppm to 750 ppm Vitamin C; and from 1.5 ppm to 50 ppm polyphenol; wherein, all percentages by weight are based on total dry weight.

An embodiment provides a kit for managing non-food allergies in a companion animal comprising two or more ingredients that, when combined together and optionally with additional ingredients that are not a part of the kit, yield a composition that comprises: one or more omega-3 fatty acids, one or more omega-6 fatty acids, and one or more omega-9 fatty acids, in relative amounts to produce a total omega-3 to total omega-6 fatty acid to total omega-9 fatty acid ratio of from about 0.9:2.0:2.0 to about 3.0:5.0:5.0, and a total omega-6 fatty acid content of from about 1.5 percent by weight to about 12 percent by weight; from 0.01 percent by weight to 0.12 percent by weight alpha-lipoic acid; from 0.1 percent by weight to 15 percent by weight of egg product; from 200 IU/kg to 1,300 IU/kg Vitamin E; from 30 ppm to 750 ppm Vitamin C; and from 1.5 ppm to 50 ppm polyphenol; wherein, all percentages by weight are based on total dry weight.

A further embodiment provides use of a composition that comprises: one or more omega-3 fatty acids, one or more omega-6 fatty acids, and one or more omega-9 fatty acids, in relative amounts to produce a total omega-3 to total omega-6 fatty acid to total omega-9 fatty acid ratio of from about 0.9:2.0:2.0 to about 3.0:5.0:5.0, and a total omega-6 fatty acid content of from about 1.5 percent by weight to about 12 percent by weight; from 0.01 percent by weight to 0.12 percent by weight alpha-lipoic acid; from 0.1 percent by weight to 15 percent by weight of egg product; from 200 IU/kg to 1,300 IU/kg Vitamin E; from 30 ppm to 750 ppm Vitamin C; and from 1.5 ppm to 50 ppm polyphenol; wherein, all percentages by weight are based on total dry weight to prepare a food for managing non-food allergies in a companion animal. This may be as part of a treatment regimen, for example, prescribed by a veterinarian.

Further, the invention is directed to the use of a pet food composition in managing non-food allergies in companion animals and means for communicating the use.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION

Figure 1:
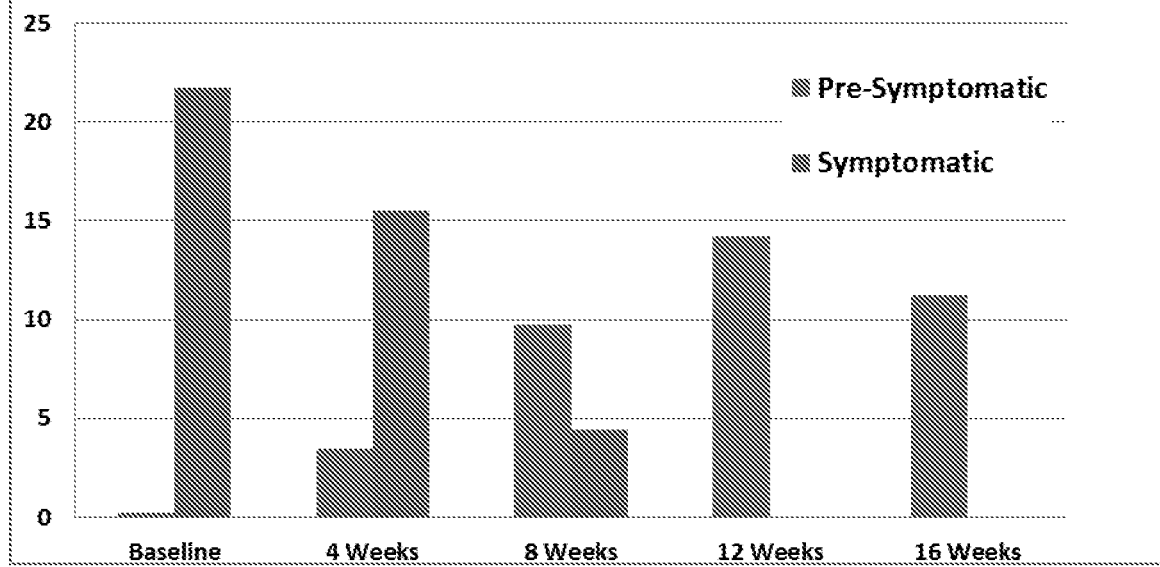
FIG. 1 is a graph of the Mean Skin Health Scores from Example 2.

The following description of the preferred embodiment(s) is merely exemplary in nature and is in no way intended to limit the invention, its application, or uses.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

The invention is directed to a food composition comprising a combination of nutrients effective in reducing skin redness, repairing skin, improving hair texture and reducing hair oiliness. In addition, the food composition is effective in reducing itching in pets that exhibit symptoms related to environmental allergies, and can delay the onset of clinical signs or reduce the severity of clinical signs if the composition is administered before a companion animal is exposed to environmental allergens. The recurrence rate for seasonal atopic dermatitis is high. Therefore, the identification of periods when dogs will be vulnerable can be established based upon an understanding of their past seasonal experiences.

Atopic dermatitis is an inflammatory, chronic skin disease associated with allergies, triggered by non-topical allergen insult, such as pollen inhalation. The term atopic is used to indicate it does not arise from direct topical contact exposure of the inflamed area to the allergen. Allergic contact dermatitis may result from direct skin exposure to the allergen. Symptoms of dermatitis in dogs include pruritus, lichenification, excoriation, erythema and alopecia. Observable behaviors in dogs suffering from dermatitis include itching, licking, rubbing and scratching.

Pruritus is the medical term for itching. It is common in many types of skin disorders. Lichenification describes the presence of thick, leathery skin, usually the result of constant scratching and rubbing. Lichenification is a common consequence of atopic dermatitis and other pruritic (itchy) disorders. With prolonged rubbing or scratching, the outer layer of the skin (the epidermis) becomes hypertrophied (overgrown) and this results in thickening of the skin and exaggeration of the normal skin markings, giving, the skin a leathery bark-like appearance. Excoriation is a term used to describe skin damage/removal as a result of excessive scratching, or biting, at the itchy area of skim. Erythema multiforme is a skin condition that is characterized by raised spots or other skin lesions. Alopecia is the loss of hair, which may result from skin irritation.

Early intervention in canine atopic dermatitis results in improved mean peak skin health and pruritus scores. Incorporating the food according to the invention into a pretreatment protocol, as part of a multimodal strategy to manage dogs with atopic dermatitis, may result in delayed or reduced use of medication. In this exemplary method, food according to the invention is fed to the animal during an induction period prior to the expected exposure of the animal to the allergen. The induction period can be from 1 week to 10 weeks, from 2 weeks to 8 weeks, from 3 weeks to 6 weeks, optionally about 4 weeks.

Managing non-food allergies can comprise pre-treatment with nutrition in the form of the food of the invention to support skin repair and reduction of immune response. Such pretreatment, along with frequent monitoring for symptoms of non-food allergies, can limit and/or delay the need for medications which may otherwise have been needed as a part of early intervention upon presentment of symptoms of non-food allergic response.

Nutritional management of canine atopic dermatitis helps the body prepare against the onslaught of antigens either within the home or outside. This requires a building up and restoration of the skin barrier, and reduction of the over reactive response of the body to external antigens.

The food provided is a blend of fats and oils, whole egg, antioxidants and sources of polyphenols formulated to help modulate the immune response to allergens. The functional goal of the inclusion of these nutrients is to help stabilize mast and inflammatory cells, thereby decrease histamine and cytokine release. Components within eggs have been shown to have immunomodulation and anti-oxidant activity among other benefits.

Polyphenols have various interesting effect on the immune system. For example, flavonoids have anti-inflammatory and antioxidant activity, and also can stabilize mast cells.

Nutritional management for canine atopic dermatitis inhibits the inflammatory response, stabilizes the skin barrier and supports skin and coat health. Invisible inflammation is present in patients who have skin barrier dysfunction and can be addressed using nutrition and pharmaceuticals. Unhealthy skin, including the ear canal, can be addressed externally through the use of topical anti-inflammatory medications and gentle cleansing. Unhealthy skin can also be addressed through nutrition to support healing and growth of a strong, resilient hair coat.

Plant based foods such as green tea, fruits, some herbs and green vegetables are rich in polyphenols which act as antioxidants, induce antioxidant enzymes such as glutathione peroxidase and superoxide dismutase and have been found to modulate cell signaling pathways. In human and laboratory animal studies, polyphenols have been found to play an inhibiting role in the presentation of allergens to the immune system and an inhibitory role in T cell release of cytokines, inhibition of B cell production of IgE and inhibition of degranulation by mast cells. In addition, polyphenols have anti-oxidant activity limiting the free radical cellular injury which may occur during allergic insults.

Vitamin E, antioxidants and omega-3 fatty acids also play a role. Vitamin E plays a vital role in protecting skin lipids from peroxidation secondary to exposure to UV radiation, inflammation or infection. Dietary alpha tocopherol increases serum vitamin E levels and serum vitamin E correlates with skin levels of vitamin E. The food according to the invention contains vitamin E in excess of the above recommended amount and also contains other anti-oxidant sources including vitamin C, green tea as source of catechins and lipoic acid.

Gene expression and metabolic pathway analysis are useful techniques to identify ingredients and nutrients which positively affect pathways of interest for a particular disease. Metabolic pathway analysis uses complex modeling of network-based pathways to interpret gene expression and metabolite data. In the exemplary case of canine atopic dermatitis, we identified ingredients that target inflammation, the immune system and histamine related pathways. Therefore, the food may also contain beneficial fats and complex carbohydrate sources shown in cell culture studies to have a positive effect on metabolic pathways associated with inflammation, the immune system and histamine.

Achieving healthy skin and hair coat requires a complex balance of macro and micronutrients. Protein, Vitamins E, omega-3 and omega-6 fatty acids and their ratio to one another, and minerals such as zinc and copper all contribute to growth and healing of the epidermis, dermis, collagen and pigmentation. Both omega-6 and omega-3 fatty acids play important roles in skin and systemic health. The essential fatty acids, cis-linoleic and alpha-linolenic represent omega-6 and omega-3 fatty acid families respectively. In companion animal atopic dermatitis, both omega-6 and omega-3 fatty acids are important in skin healing and its resistance to producing inflammatory cytokines in the face of allergic insult. It is well known that omega-3 fatty acids result in less inflammatory cytokines and as the relative amount of omega-3 fatty acids in the diet increases, more prostaglandins of the 3 series and leukotrienes of the 5 series are produced in cells. Omega-9 fatty acids are thought to impact signaling cascades that affect inflammation and cell growth.

The combination of nutrients in the pet food, according to an embodiment of the invention, includes (all percentages express weight percent based on total dry food weight, unless otherwise specified):

Total dietary fat levels from sources like chicken, pork, and/or beef fat, of from 8% to 25%, from 10% to 20%, from 11% to 19%, from 12% to 18%, from 13% to 17%, from 14% to 16%;

Omega 3, 6 and 9 fatty acids are present in a ratio of from 0.5:2.0:2.0 to 3.0:5.0:5.0, from 0.7:2.0:2.0 to 1.2:2.0:2.0; optionally about 0.8:2.0:2.0 to 1.1:2.0:2.0, optionally about 0.9:2.0:2.0 to 1.0:2.0:2.0. The fatty acids come from sources like soybean oil, flaxseed, chicken fat, pork fat, beef fat, olive oil, sunflower oil, corn oil, coconut oil, and/or fish oil. Fatty acids are long carbon chains with a methyl group at one end. Polyunsaturated fatty acids have multiple double bonds. The fatty acids that have the first double bond three carbons away from the methyl group are the omega-3 (or n-3) series. The omega-6 (or n-6) series of polyunsaturated fatty acids have the first double bond six carbons from the methyl group. In mammals, polyunsaturated omega-3 and omega-6 fatty acids are essential fatty acids ("EFAs") because they cannot be synthesized de novo by mammals. Members of the omega-6 family include, for example, linoleic (18:2n-6), gamma-linolenic (18:3n-6), dihomogammalinolenic (20:3n-6), and arachidonic acid (20:4n-6). Members of the omega-3 family include, for example, alpha-linolenic (18:3n-3), eicosatetraenoic (20:4n-3), eicosapentaenoic (20:5n-3), and docosahcxaenoic acid (22:6n-3). In the skin, EFAs are principally found in phospholipids. The high degree of unsaturation of EFAs bestows fluidity to phospholipids at physiologic temperatures, allowing conformational changes to occur. One of the skin-related functions of EFAs is the incorporation of linoleic acid into the ceramides of the lipid portion of the epidermal cornified envelope. This envelope serves a barrier function to prevent loss of water and other nutrients. EFAs are a source of energy for the skin and serve as precursors to a variety of potent, short-lived molecules including prostaglandins, leukotrienes, and their metabolites. In some embodiments, the composition comprises an amount of linoleic acid that is equal to or higher than the minimum allowance recommended by the Association of American Feed Control Officials ("AAFCO"). In some embodiments, the composition comprises an amount of linoleic acid that is up to about 200% higher, up to about 300% higher, up to about 400% higher, up to about 500% higher, up to about 600% higher, up to about 700% higher, up to about 800% higher, up to about 900% higher, up to about 1000% higher, or up to about 1100% higher than the respective AAFCO minimum allowance. The AAFCO's minimum linoleic acid allowance for growth, reproduction, and maintenance of dogs is 1% on a dry matter basis (presuming that the energy density of the diet is 3.5 kcal ME/g dry matter). Therapeutic non-zero amounts of various ingredients can generally be determined by reference to such dietary guidelines and other materials within the general knowledge of food scientists and veterinary practitioners. In some embodiments:

The amount of egg product, such as dried egg present is from 0.1% to 15%, from 0.2% to 14%, from 0.3% to 13% from 0.4% to 12%, from 0.5 to 11%, from 0.7 to 10%, from 0.8% to 9%, from 0.9% to 8%, from 1% to 7%, from 2% to 6%, from 3% to 5%.

The amount of Vitamin E present is from 200 IU/kg to 1,300 IU/kg, from 300 IU/kg to 1,200 IU/kg, 400 IU/kg to 1,100 IU/kg, from 500 IU/kg to 1,000 IU/kg, from 600 IU/kg to 800 IU/kg.

The amount of Vitamin C present is from 30 ppm to 750 ppm, from 50 ppm to 700 ppm, from 75 ppm to 600 ppm, from 100 ppm to 500 ppm.

The amount of dietary polyphenol, such as quercetin present is from 1.5 ppm to 50 ppm, from 3 ppm to 40 ppm, from 4 ppm to 30 ppm, from 5 ppm to 25 ppm, from 8 ppm to 20 ppm, from 10 ppm to 15 ppm.

Quercetin sources include green tea extract, pea powder, apple powder, cranberry powder, carrot powder, broccoli powder, rosemary extract, citrus extract, schinopsis extract, eugenia extract, and curcuma extract.

The food composition includes dry and wet (loaf, minced, stew) compositions, including nutritionally complete diets, snacks and treats.

In another aspect, the present invention provides an article of manufacture, such as for example a kit comprising elements which can be assembled to form the composition. In some embodiments, the kit comprises in separate containers in a single package or in separate containers in a virtual package, as appropriate a composition of the present invention or two or more ingredients, that, when combined together and optionally with additional ingredients that are not a part of the kit, yield a composition comprising one or more omega-3 fatty acids, one or more omega-6 fatty acids, and one or more omega-9 fatty acids, in relative amounts to produce a total omega-3 to total omega-6 fatty acid to total omega-9 fatty acid ratio of from about 0.9:2.0:2.0 to about 3.0:5.0:5.0, and a total omega-6 fatty acid content of from about 1.5 percent by weight to about 12 percent by weight; from 1 percent by weight to 12 percent by weight alpha-lipoic acid; from 0.1 percent by weight to 15 percent by weight of egg product; from 200 IU/kg to 1,300 IU/kg Vitamin E; from 30 ppm to 750 ppm Vitamin C; and from 1.5 ppm to 50 ppm polyphenol; wherein, all percentages by weight are based on total dry weight and at least one of (1) instructions for feeding the composition to an animal, (2) instructions for making a composition of the present invention by combining the two or more ingredients, (3) one or more agents for managing non-food allergies, and (4) instructions for administering the agents in conjunction with the composition. The term "single package" generally means that the components of a kit are physically associated in or with one or more containers and considered as a unit of manufacture, distribution, sale, or use.

Containers include, but are not limited to, bags, boxes, bottles, cans, shrink wrap packages, stapled or otherwise fixed components, or combinations thereof. A single package can be, for example, containers or individual food compositions physically associated such that they are considered a unit for manufacture, distribution, sale, or use. The term "virtual package" generally means that the components of a kit are associated by directions on one or more physical or virtual kit components instructing the user how to obtain additional components, e.g., in a bag containing one component and directions instructing the user to go to a website, contact a recorded message, view a visual message, or contact a caregiver to obtain instructions on how to use the kit. When the kit comprises a virtual package, the kit is limited to instructions in a virtual environment with one or more physical kit components.

In another aspect, the present invention provides a means for communicating information about or instructions for one or more of (1) using a composition of the present invention for managing non-food allergies, (2) using a composition of the present invention in conjunction with one or more agents for improving skin health, improving pelage quality, and/or promoting the health or wellness of an animal, and (3) using a kit of the present invention for managing non-food allergies comprising a document, digital storage media, optical storage media, audio presentation, a web app, or visual display containing the information or instructions. In certain embodiments, the communicating means comprises a document, digital storage media, optical storage media, audio presentation, or visual display containing the information or instructions. Preferably, the communication means is a displayed web site, a web app, or a brochure, product label, package insert, advertisement, or visual display containing such information or instructions. Useful information or instructions include, for example, (1) information and instructions how to use a composition, method, or kit of the present invention and (2) contact information for animal caregivers if they have a question about the invention and its uses.

In one embodiment the pet food composition, as described herein, may be prescribed by a veterinarian as part of a treatment regimen. In a further embodiment, the veterinarian or pet owner may track the efficacy of the treatment regimen through observation and/or other monitoring, such as a wearable device on dogs which monitors behaviors associated with allergies, for use in combination with the food according to the invention.

EXAMPLES

Example 1

A double blind study was performed to determine the impact of a test food (T) comprising ingredients designed to have immune modulating effects on seasonal atopy versus a control food (C). Dogs with a history of, but without current clinical signs of seasonal atopy were recruited in the spring from general veterinary practices in the United States. Dogs currently on foods designed for adverse food reactions or that had undergone desensitization therapy were excluded. Eligible dogs were randomly assigned to the T or C groups, and evaluated by their veterinarian at 0, 4, 8, 12 and 16 weeks. Medications prescribed, and dosing information was collected. Only oclacitinib, which was not uniformly available, was disallowed during the study.

Veterinarians scored for pruritus (0-none to 4-severe) and a used a skin score visual atlas to grade 27 regions (0-none to 4-severe) for erythema, lichenification, excoriation and alopecia. Dogs with incomplete data, without clinical signs, or a CADESI >0 or at baseline, were eliminated from the data set. Thirty-six dogs (19 T, 16 C) were included in the final analysis. Medications were administered to 15/16 (93.75%) of C vs. 13/19 (68.42%)% of T dogs. Most commonly, a topical containing a glucocorticoid, systemic antihistamine, a systemic glucocorticoid and/or a systemic immunomodulator was administered. A survival analysis was performed considering time until first prescribed day for topical (99±6.5 d C, 93.6±8.8 d T) medications, antihistamine (54.3±3.8 d C, 60.2±5.2 d T) and systemic glucocorticoids (83.2±8.1 d C, 102.6±5.6d T). As shown in Table 1 below, results were similar for topical medications and were numerically lower for both systemic medications in treated dogs. Fewer Test food fed dogs received each type of medication—topical (44% C, 42% T), antihistamine (44% C, 26% T),systemic glucocorticoids (50% C, 37% T) and systemic immunomodulator (6% C, 0% T). Overall fewer test food fed dogs received any medication (93.75% C, 68.42% T). The test food contributed to delayed and decreased medical intervention.

TABLE 1

Medication Data

| Food | Patient | Systemic antihistamine | Topical glucocorticoid | Systemic glucocorticoid | Systemic Immunomodulator (cyclosporine) |
|---|---|---|---|---|---|
| Control | C84-DT-003-P | | YES | | |
| Control | C84-EH-002-P | | YES | YES | |
| Control | C84-KR-005-P | | | YES | |
| Control | C84-KR-008-P | | YES | YES | |
| Control | C84-KR-010-P | | YES | | |
| Control | C84-KR-011-P | | | YES | |
| Control | C84-LB-002-P | YES | | | |
| Control | C84-LB-007-P | YES | YES | | |
| Control | C84-LB-010-P | YES | | | |
| Control | C84-LB-013-P | YES | | YES | YES |
| Control | C84-MP-010-P | YES | | YES | |
| Control | C84-MP-012-P | YES | | YES | |
| Control | C84-MP-014-P | YES | YES | | |
| Control | C84-SH-009-P | | | YES | |
| Control | C84-SH-011-P | | | | |
| Control | C84-SR-005-P | | | YES | |
| | Percentage n =16 | 44%% | 44% | 50% | |
| | | Overall Percentage 15/16 = 94.75% | | | |
| Test | C84-DK-002-P | | YES | YES | |
| Test | C84-DT-004-P | | | | |
| Test | C84-DT-005-P | | YES | | |
| Test | C84-DT-007-P | | | | |
| Test | C84-DT-012-P | | | YES | |
| Test | C84-DT-013-P | | YES | | |
| Test | C84-EH-001-P | YES | YES | | |
| Test | C84-EH-003-P | | YES | | |
| Test | C84-KR-006-P | | YES | YES | |
| Test | C84-KR-007-P | | | YES | |
| Test | C84-LB-006-P | YES | | YES | |

TABLE 1-continued

Medication Data

| Food | Patient | Systemic antihistamine | Topical glucocorticoid | Systemic glucocorticoid | Systemic Immunomodulator (cyclosporine) |
|---|---|---|---|---|---|
| Test | C84-LB-008-P | YES | | YES | |
| Test | C84-MP-008-P | | YES | | |
| Test | C84-MP-017-P | YES | YES | YES | |
| Test | C84-RS-008-P | | | | |
| Test | C84-RS-010-P | | | | |
| Test | C84-SG-002-P | | | | |
| Test | C84-SH-003-P | YES | | | |
| Test | C84-SR-004-P | | | | |
| | Percentage n = 19 | 26% | 42% | 37% | 0% |
| | Overall Percentage 13/19 = 68.42% | | | | |

Example 2

A case series was performed to determine the impact of the food composition according to the present invention on clinical signs of seasonal atopy. Dogs with a history of and current clinical signs of atopy were recruited from general veterinary practices in the United States and evaluated by their veterinarian and owner at 0, 4 and 8 weeks. Medications could be prescribed except oclacitinib, which was not uniformly available. Veterinarians scored for pruritus and a used a modified CADESI to grade 27 body regions (0-none to 4-severe). Owners evaluated atopy related behaviors with a visual scale of "none" to "all of the time." The continuum was converted to a 0-100 score and answered questions concerning hair coat and skin. Twenty out of 27 enrolled dogs completed the study; 7 were dismissed for compliance (5) or diarrhea/acceptance (2). Medication was administered to 19/20 dogs, most commonly topical with a glucocorticoid, systemic antihistamine and/or a glucocorticoid was administered. At 8 weeks, 75% had a lower CADESI, 15% increased and 75% had decreased pruritus, 5% increased (Tables 2, 3 and 4

Example 2A

Figure 2:
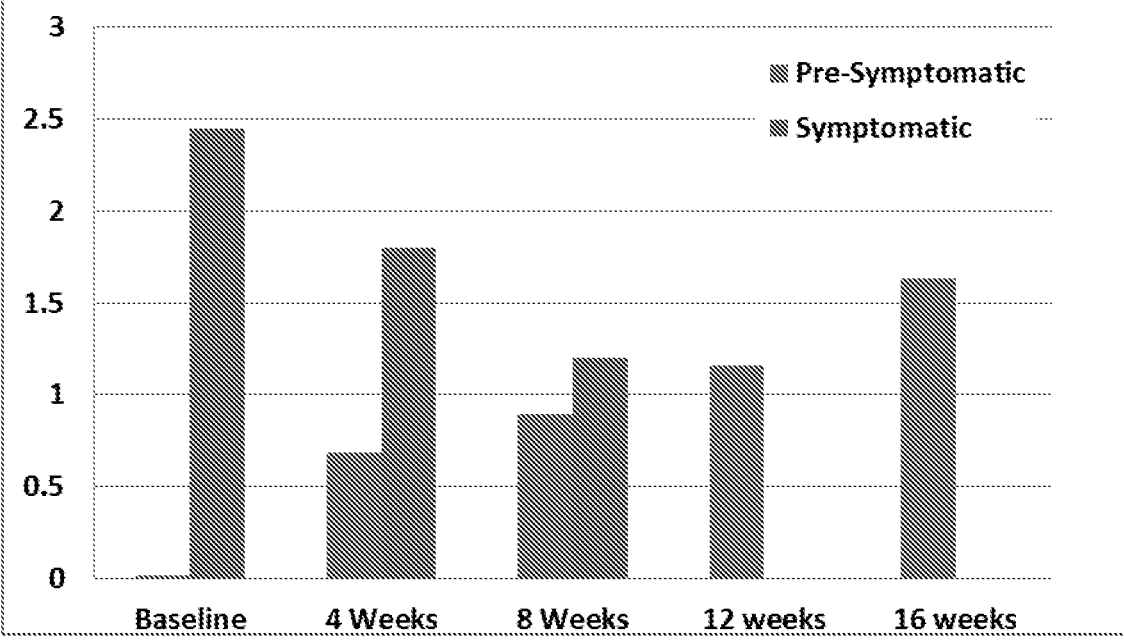
FIG. 2 is a graph of the Mean Pruritus Scores from Example 2.

FIGS. 1 and 2 illustrate the surprising improvement in Total Skin Health and Pruritus Scores from dogs enrolled in the studies outlined in Example 1 and Example 2. Peak skin and pruritus scores in the Example 1 study were lower for dogs consuming the food invention and dogs in both studies showed improvement. Dogs in Example 1 received pretreatment with food of the invention as part of multimodal therapy (n =19) versus 20 dogs that were started on the food as part of multimodal therapy after becoming symptomatic as described in Example 2.

TABLE 2

Total CADESI (Canine Atopic Dermatitis Extent and Severity Index Score)

| | Visit | | |
|---|---|---|---|
| Patient ID | Screening n-20 | Week 4 n = 20 | Week 8 n = 20 |
| C84-DT-001-S | 4 | 4 | 12 |
| C84-DT-002-S | 9 | 0 | 2 |
| C84-KR-001-S | 11 | 9 | 4 |
| C84-KR-002-S | 58 | 12 | 50 |
| C84-KR-004-S | 8 | 0 | 0 |
| C84-MP-002-S | 0 | 0 | 0 |
| C84-MP-003-S | 5 | 6 | 2 |
| C84-MP-005-S | 24 | 23 | 2 |
| C84-MP-006-S | 68 | 71 | 4 |
| C84-MP-007-S | 7 | 6 | 1 |
| C84-MP-015-S | 81 | 51 | 34 |
| C84-RS-005-S | 11 | 25 | 8 |
| C84-RS-006-S | 65 | 49 | 30 |
| C84-RS-007-S | 2 | 1 | 2 |
| C84-SH-001-S | 3 | 10 | 10 |
| C84-SH-005-S | 8 | 0 | 2 |
| C84-SH-006-S | 34 | 16 | 5 |
| C84-SH-007-S | 6 | 0 | 2 |
| C84-SH-008-S | 12 | 6 | 13 |
| C84-SR-003-S | 18 | 14 | 0 |
| Mean: | 21.70 | 15.15 | 9.15 |
| StdDev: | 25.28 | 19.88 | 13.46 |

| | Week 4 | Week 8 |
|---|---|---|
| Increased | 4 (20%) | 3 (15%) |
| Decreased | 14 (70%) | 15 (75%) |
| Same | 2 (10%) | 2 (10%) |

TABLE 3

Pruritus score per animal per visit.

| | Visit | | |
|---|---|---|---|
| Patient ID | Screening n-20 | Week 4 n = 20 | Week 8 n = 20 |
| C84-DT-001-S | 2 | 2 | 2 |
| C84-DT-002-S | 3 | 1 | 1 |
| C84-KR-001-S | 3 | 2 | 1 |
| C84-KR-002-S | 3 | 1 | 3 |
| C84-KR-004-S | 2 | 0 | 0 |
| C84-MP-002-S | 3 | 2 | 3 |
| C84-MP-003-S | 2 | 1 | 1 |
| C84-MP-005-S | 3 | 2 | 0 |
| C84-MP-006-S | 3 | 3 | 1 |
| C84-MP-007-S | 2 | 2 | 1 |
| C84-MP-015-S | 4 | 3 | 2 |
| C84-RS-005-S | 2 | 2 | 1 |
| C84-RS-006-S | 3 | 3 | 2 |
| C84-RS-007-S | 1 | 1 | 1 |
| C84-SH-001-S | 1 | 3 | 2 |
| C84-SH-005-S | 2 | 1 | 0 |
| C84-SH-006-S | 3 | 2 | 0 |
| C84-SH-007-S | 1 | 1 | 0 |
| C84-SH-008-S | 3 | 2 | 2 |
| C84-SR-003-S | 3 | 2 | 1 |
| Mean: | 2.45 | 1.80 | 1.20 |
| StdDev: | 0.83 | 0.83 | 0.95 |

| | Week 4 | Week 8 |
|---|---|---|
| Increased | 1 (5%) | 1 (5%) |
| Decreased | 12 (60%) | 15 (75%) |
| Same | 7 (35%) | 4 (20%) |

TABLE 4

Erythema Score Per Animal Per Visit

| Patient ID | Screening n-20 | Week 4 n = 20 | Week 8 n = 20 |
|---|---|---|---|
| C84-DT-001-S | 4 | 4 | 9 |
| C84-DT-002-S | 4 | 0 | 1 |
| C84-KR-001-S | 9 | 3 | 2 |
| C84-KR-002-S | 22 | 2 | 22 |
| C84-KR-004-S | 6 | 0 | 0 |
| C84-MP-002-S | 0 | 0 | 0 |
| C84-MP-003-S | 5 | 6 | 2 |
| C84-MP-005-S | 5 | 4 | 0 |
| C84-MP-006-S | 24 | 28 | 4 |
| C84-MP-007-S | 5 | 4 | 1 |
| C84-MP-015-S | 28 | 4 | 4 |
| C84-RS-005-S | 6 | 13 | 4 |
| C84-RS-006-S | 30 | 19 | 8 |
| C84-RS-007-S | 2 | 1 | 2 |
| C84-SH-001-S | 2 | 3 | 2 |
| C84-SH-005-S | 8 | 0 | 2 |
| C84-SH-006-S | 13 | 2 | 1 |
| C84-SH-007-S | 6 | 0 | 2 |
| C84-SH-008-S | 6 | 2 | 10 |
| C84-SR-003-S | 9 | 4 | 6 |
| Mean: | 9.70 | 4.95 | 4.10 |
| StdDev: | 8.93 | 7.15 | 5.15 |

|  | Week 4 | Week 8 |
|---|---|---|
| Increased | 4 (20%) | 2 (10%) |
| Decreased | 14 (70%) | 14 (70%) |
| Same | 2 (10%) | 4 (20%) |

Veterinarian mean scores for other parameters are shown in Table 5 and demonstrate improved scores for hair coat shine (Scale: 1-Extremely Dull to 7-Extremely Shiny), coat texture (1-Extremely Coarse or Brittle to 7-Extremely Soft), shedding (1-Excessive to 5-None), skin healing (1-Poor to 5-Excellent), dander (1-Excessive to 5-None), hair regrowth (1-Poor-5-Excellent), overall coat quality (1-Poor to 5-Excellent) and overall skin quality (1-Poor to 5-Excellent). The scoring ranges including qualitative descriptors for range endpoints are provided above, and the numerical values appear in Table 5, below.

TABLE 5

| Veterinarian Assessment | Baseline | Week 4 | Week 8 | Range of Responses |
|---|---|---|---|---|
| Coat Shine | 4.10 | 4.25 | 5.05 | 1 to 7 |
| Coat Texture | 4.70 | 4.65 | 5.20 | 1 to 7 |
| Shedding | 4.00 | 4.45 | 4.50 | 1 to 5 |
| Skin Healing | 2.33 | 2.14 | 3.56 | 1 to 5 |
| Dander | 4.25 | 4.65 | 4.75 | 1 to 5 |
| Hair Regrowth | 2.13 | 2.00 | 3.11 | 1 to 5 |
| Overall Coat Quality | 3.00 | 3.00 | 3.55 | 1 to 5 |
| Overall Skin Quality | 2.80 | 3.05 | 3.35 | 1 to 5 |

The majority of dogs had improved clinical signs (Table 6) as mean owner scores improved for skin redness, itching and scratching, licking, head shaking, coat shine, face rubbing and pet's condition as disruptive; 65% of owners believed the food was somewhat to highly effective in reducing licking and scratching and 70% wanted to continue feeding the new food.

TABLE 6

Pet Owner mean scores for signs of environmental allergies

| Pet Owner Question | Mean Score 0-Extreme 100-None | | | | | |
|---|---|---|---|---|---|---|
|  | Baseline | Week 1 | Week 2 | Week 3 | Week 4 | Week 8 |
| Skin Redness | 57.9 | 64.7 | 75.4 | 75.6 | 75.9 | 74.5 |
| Itching and scratching | 39.6 | 44.2 | 56.4 | 53.8 | 54.0 | 59.1 |
| Licking | 36.7 | 40.8 | 57.5 | 55.0 | 52.5 | 60.4 |
| Head Shaking | 67.1 | 70.1 | 76.4 | 79.3 | 78.6 | 78.9 |
| Coat Shine | 58.3 | 56.4 | 64.3 | 63.5 | 68.4 | 64.5 |
| Face Rubbing | 61.2 | 63.1 | 73.5 | 75.4 | 68.2 | 71.5 |
| How Disruptive is Skin Condition | 53.6 | 54.8 | 65.6 | 64.4 | 67.6 | 70.9 |

Example 3

Figure 3:
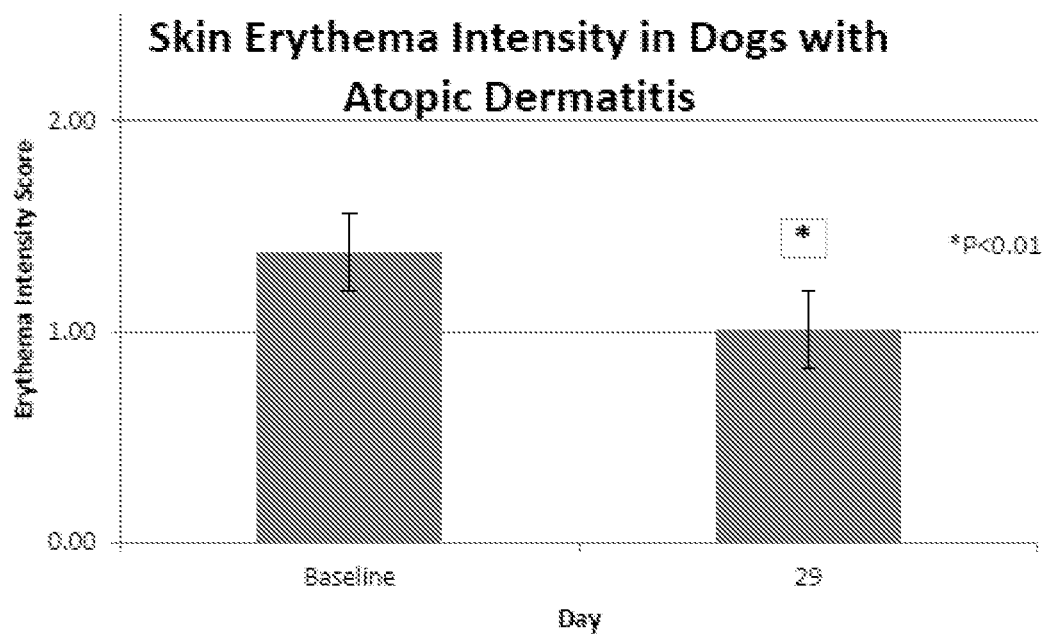
FIG. 3 presents graphs of the results of Example 3, depicting the baseline results and after 29 days of feeding for Skin Erythema Intensity in dogs with atopic dermatitis.
Figure 4:
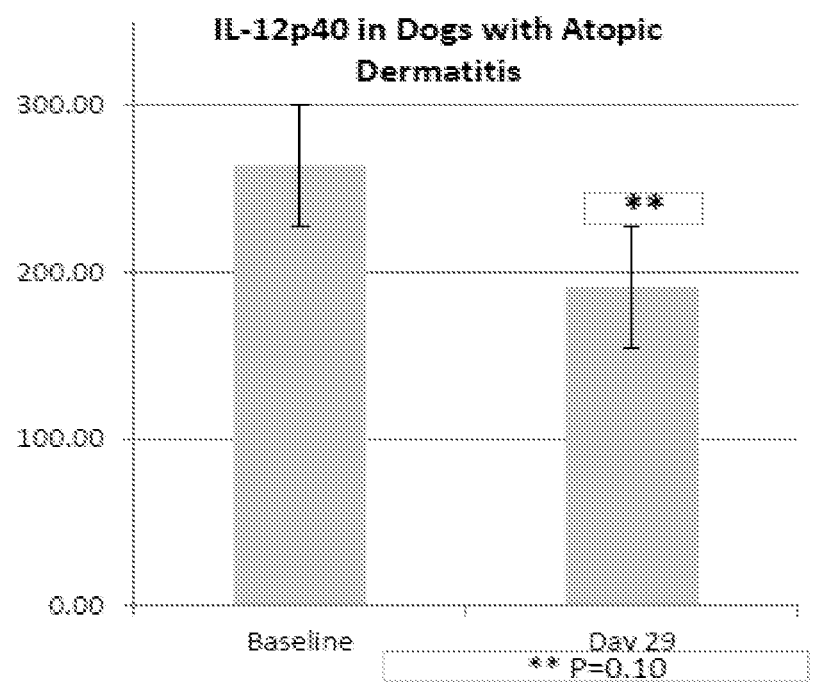
FIG. 4 presents a graph which shows the IL-12p40 results of Example 3.
Figure 5:
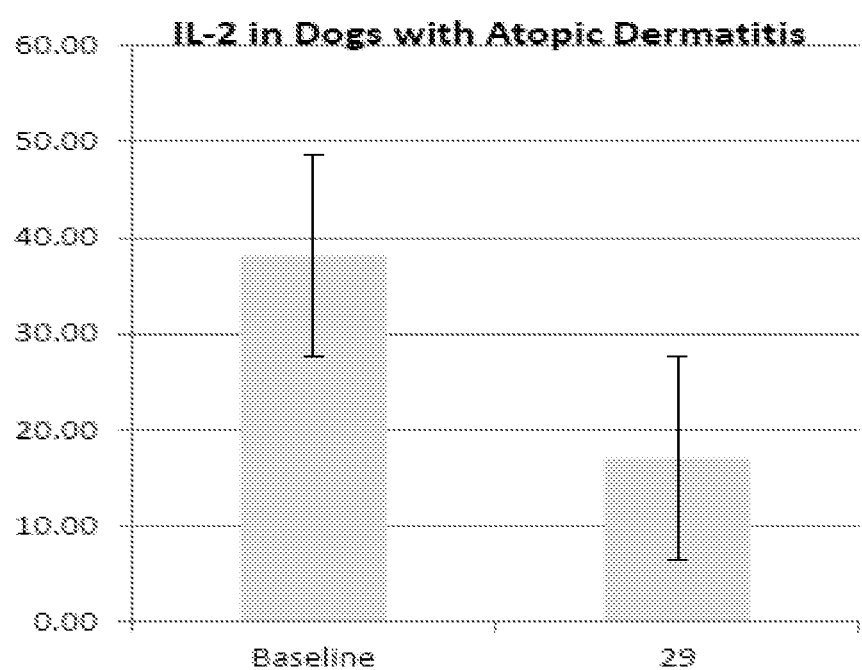
FIG. 5 presents a graph which shows the IL-2 results of Example 3.
Figure 6:
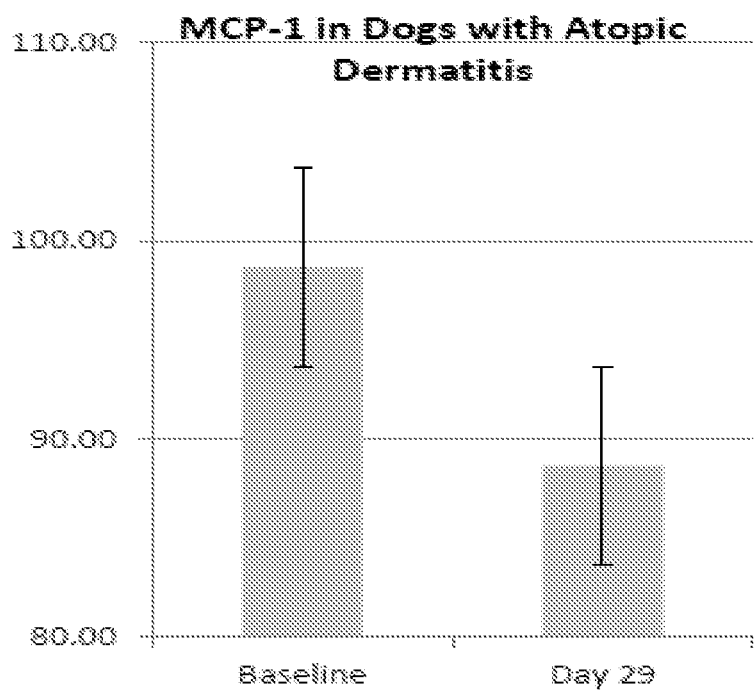
FIG. 6 presents a graph which shows the MCP-1 results of Example 3.

Twenty five adult dogs (12 neutered males, 11 spayed females, 2 intact females, mean age 8.5 years) with a history of atopic dermatitis that were showing active signs of skin erythema were fed a complete and balanced dry test dog food for 29 days. The test food contained 4% total omega-6 fatty acids, 1.8% total omega-3 fatty acids, 900 IU/kg alpha tocopherol on a dry matter basis as well as eggs and multiple botanical ingredients as sources of polyphenols all of which were intended to reduce systemic inflammation and immune system mediators in an effort to reduce skin irritation and redness in these dogs. Skin erythema intensity was scored by a veterinarian at baseline and after 29 days of feeding the test food. Scores across 11 regions of each dogs' body were made using a scale of 0=none, 1=mild, 2=moderate and 3=severe erythema. Food intake was measured daily, body weights were collected weekly, and blood samples for cytokine analysis were collected at baseline and on day 29. Food intake and body weight were unchanged during the feeding period. Mean skin erythema intensity score at baseline was 1.4 indicating that overall skin erythema was mild to moderate in these dogs, although some dogs had selected regions of their body with severe skin redness. As shown in FIG. 3, mean skin erythema intensity was significantly reduced to 1.1 ($P<0.01$) after 29 days of feeding with 16 dogs (64%) showing a decline in skin erythema intensity score and 8 dogs with clinical skin redness at baseline that had no visible skin redness after consuming the test food. Cytokines analyzed were TNF-alpha, VEGF-A, IFN-gamma, NGF-beta, SCF, MCP-1, IL-2, IL-6, IL-8, IL-10, and IL-12p40. TNF-alpha, IFN-gamma, NGF-beta, IL-6 and IL-10 were below assay detection limits. There were no significant changes from baseline to day 29 for VEGF-A, SCF and IL-8. FIGS. 4-6 present graphs of the results, which shows that IL-12p40 was significantly lower ($P=0.10$) and MCP-1 and IL-2 were also lower compared to baseline. The test food containing anti-inflammatory ingredients and antioxidants had a generally positive effect in lowering pro-inflammatory cytokines and importantly significantly reducing clinical signs of skin redness in dogs with atopic dermatitis.

TABLE 7

Dry Food Formulation:

| Ingredient Composition of Test Food | % of formula |
|---|---|
| Grains and fibers | 59.8 |
| Animal & vegetable proteins | 18.6 |
| Fats & oils* | 9.3 |
| Flavors & nutritional balancing ingredients | 5.8 |
| Dried egg** | 4.0 |
| Minerals mixture | 1.1 |
| Fruits, vegetables, green tea, lipoic acid, herb and spice extracts*** | 0.9 |
| Vitamins mixture**** | 0.7 |
| Total | 100 |

*(sources of omega-3, omega-6 & omega-9 fatty acids); (source of egg product); *(source of polyphenols); ****(source vitamin E, vitamin C).

Ingredients:

Rice, Chicken Meal, Sorghum, Barley, Pea Protein, Eggs, Soybean Oil, Flaxseed, Chicken Liver Flavor, Oats, Beet Pulp, Fish Oil, Pork Liver Flavor, Lactic Acid, Chicken Fat, Potassium Chloride, Lipoic Acid, Choline Chloride, Salt, Vitamin E, Vitamin C, Niacin, Thiamine, Vitamin A, Calcium Pantothenate, Vitamin B12, Pyridoxine Hydrochloride, Riboflavin, Biotin, Folic Acid, Vitamin D3, Calcium Carbonate, Green Peas, Apples, Cranberries, Carrots, Ferrous Sulfate, Zinc Oxide, Copper Sulfate, Manganous Oxide, Calcium Iodate, Sodium Selenite, Taurine, Herb extracts, Spice Extracts, Mixed Tocopherols, Broccoli, Beta-Carotene.

TABLE 8

| Test Food Nutrient Content | Expressed on 100% dry matter basis |
|---|---|
| Overall nutrients | |
| Protein, % | 23.0 |
| Fat, % | 15.2 |
| Omega-3 Fatty Acids, % | 1.8 |
| Omega-6 Fatty Acids, % | 4.0 |
| Omega-9 Fatty Acids, % | 4.0 |
| Ratio omega 3:omega 6:omega 9 | 0.9:2:2 |
| Vitamin E (alpha tocopherol), IU/kg | 1097 |
| Crude Fiber, % | 1.7 |
| Ash, % | 5.7 |
| Carbohydrate, % | 54.4 |
| Vitamin C (ascorbic acid), ppm | 210 |
| Alpha-lipoic Acid, ppm | 166 |

What is claimed is:

1. A composition for managing non-food allergies in a companion animal comprising:
   one or more omega-3 fatty acids, one or more omega-6 fatty acids, and one or more omega-9 fatty acids, in relative amounts to produce a total omega-3 to total omega-6 fatty acid to total omega-9 fatty acid ratio of from about 0.5:2.0:2.0 to about 3.0:5.0:5.0, and a total omega-6 fatty acid content of from about 1.5 percent by weight to about 12 percent by weight;
   from 0.1 percent by weight to 15 percent by weight of egg product;
   alpha-lipoic acid;
   quercetin; and
   Vitamin C and Vitamin E,
   wherein the Vitamin C and the Vitamin E are present in therapeutic non-zero amounts, and
   wherein the quercetin is provided by quercetin sources comprising pea powder, apple powder, cranberry powder, and broccoli powder,
   wherein all percentages by weight are on a dry matter basis of the composition.

2. The composition of claim 1, wherein the amount of the alpha-lipoic acid is from 0.01 percent by weight to 0.12 percent by weight.

3. The composition of claim 1, wherein the amount of the Vitamin E is from 200 IU/kg to 1,300 IU/kg, and the amount of Vitamin C is from 30 ppm to 750 ppm.

4. The composition of claim 1, wherein the amount of the quercetin present is from 1.5 ppm to 50 ppm.

5. The composition of claim 1, further comprising:
   from 0.01 percent by weight to 0.12 percent by weight alpha-lipoic acid;
   from 200 IU/kg to 1,300 IU/kg Vitamin E;
   from 30 ppm to 750 ppm Vitamin C; and
   from 1.5 ppm to 50 ppm quercetin,
   wherein all percentages by weight are on a dry matter basis of the composition.

6. The composition of claim 1, wherein the food has a total dietary fat content of 8 percent by weight to 25 percent by weight.

7. The composition of claim 1, wherein the composition has a total omega-3 to total omega-6 fatty acid to total omega-9 fatty acid ratio of about 1.1 to about 2.0 to about 2.0.

8. The composition of claim 1, wherein the amount of the egg product is from 0.4 weight percent to 12 weight percent.

9. The composition of claim 1, wherein the amount of the omega-6 fatty acid is from 2 weight percent to 10 weight percent.

10. A method for managing allergies to non-food allergens in a companion animal comprising feeding the animal during an induction period prior to exposure of the animal to the non-food allergen with a food composition comprising:
    one or more omega-3 fatty acids, one or more omega-6 fatty acids, and one or more omega-9 fatty acids, in relative amounts to produce a total omega-3 to total omega-6 fatty acid to total omega-9 fatty acid ratio of from about 0.5:2.0:2.0 to about 3.0:5.0:5.0, and a total omega-6 fatty acid content of from about 1.5 percent by weight to about 12 percent by weight;
    from 0.01 percent by weight to 0.12 percent by weight alpha-lipoic acid;
    from 0.1 percent by weight to 15 percent by weight of egg product;
    from 200 IU/kg to 1,300 IU/kg Vitamin E;
    from 30 ppm to 750 ppm Vitamin C; and
    from 1.5 ppm to 50 ppm quercetin,
    wherein the quercetin is provided by quercetin sources comprising pea powder, cranberry powder, and broccoli powder, and
    wherein all percentages by weight are on a dry matter basis of the composition.

11. The composition of claim 1, wherein the quercetin sources further comprise carrot powder.

12. The composition of claim 11, wherein the quercetin sources consist of the pea powder, the apple powder, the cranberry powder, the broccoli powder, and the carrot powder, and wherein the total omega-3 to total omega-6 fatty acid to total omega-9 fatty acid ratio is about 0.9:2:2.

13. The method of claim 10, wherein the food has a total dietary fat content of 8 percent by weight to 25 percent by weight.

14. The method of claim 10, wherein the composition has a total omega-3 to total omega-6 fatty acid to total omega-9 fatty acid ratio of about 1.1 to about 2.0 to about 2.0.

15. The method of claim 10, wherein the amount of the egg product is from 0.4 weight percent to 12 weight percent.

16. The method of claim 10, wherein the amount of the omega-6 fatty acid is from 2 weight percent to 10 weight percent.

17. The method of claim 10, further comprising monitoring the animal to detect symptoms of non-food allergies.

18. A kit for managing non-food allergies in a companion animal comprising two or more ingredients that, when combined together, yield a composition that comprises:
   one or more omega-3 fatty acids, one or more omega-6 fatty acids, and one or more omega-9 fatty acids, in relative amounts to produce a total omega-3 to total omega-6 fatty acid to total omega-9 fatty acid ratio of from about 0.5:2.0:2.0 to about 3.0:5.0:5.0, and a total omega-6 fatty acid content of from about 1.5 percent by weight to about 12 percent by weight;
   from 0.01 percent by weight to 0.12 percent by weight alpha-lipoic acid;
   from 0.1 percent by weight to 15 percent by weight of egg product;
   from 200 IU/kg to 1,300 IU/kg Vitamin E;
   from 30 ppm to 750 ppm Vitamin C; and
   from 1.5 ppm to 50 ppm quercetin;
   wherein the quercetin is provided by quercetin sources comprising pea powder, apple powder, cranberry powder, and broccoli powder, and
   wherein, all percentages by weight are on a dry matter basis of the composition.

19. The kit of claim 18, wherein the kit further comprises one or more agents for managing non-food allergies in a companion animal.

20. The kit of claim 19, further comprising one or more of instructions for making the composition by combining the two or more ingredients, instructions for feeding the composition to the animal, and instructions for administering the agents in conjunction with the composition.

* * * * *

UNITED STATES PATENT AND TRADEMARK OFFICE
CERTIFICATE OF CORRECTION

PATENT NO. : 10,842,169 B2  
APPLICATION NO. : 15/764345  
DATED : November 24, 2020  
INVENTOR(S) : Kathy Gross et al.

Page 1 of 1

It is certified that error appears in the above-identified patent and that said Letters Patent is hereby corrected as shown below:

In the Specification

In Column 3, Line 66, delete "skim." and insert -- skin. --, therefor.

In the Claims

In Column 14, Line 33, in Claim 7, after "1.1", delete "to about 2.0".

In Column 15, Line 8, in Claim 14, after "1.1", delete "to about 2.0".

Signed and Sealed this  
Second Day of March, 2021

Drew Hirshfeld  
*Performing the Functions and Duties of the*  
*Under Secretary of Commerce for Intellectual Property and*  
*Director of the United States Patent and Trademark Office*